United States Patent
Brenneman et al.

(10) Patent No.: US 10,010,279 B2
(45) Date of Patent: Jul. 3, 2018

(54) METHOD OF DETERMINING AN ANALYTE CONCENTRATION OF A FLUID

(71) Applicant: Ascensia Diabetes Care Holdings AG, Basel (CH)

(72) Inventors: Allen J Brenneman, Goshen, IN (US); Mihailo V. Rebec, Bristol, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

(21) Appl. No.: 15/488,886

(22) Filed: Apr. 17, 2017

(65) Prior Publication Data

US 2017/0273604 A1  Sep. 28, 2017

Related U.S. Application Data (62) Division of application No. 12/087,087, filed as application No. PCT/US2006/049039 on Dec. 21, 2006, now Pat. No. 9,668,683.

(Continued)

(51) Int. Cl.
*A61B 5/1477* (2006.01)
*A61B 5/1468* (2006.01)
(Continued)

(52) U.S. Cl.
CPC .......... *A61B 5/1477* (2013.01); *A61B 5/1468* (2013.01); *A61B 5/14507* (2013.01); *A61B 5/14532* (2013.01); *A61B 5/14546* (2013.01); *C12Q 1/006* (2013.01); *Y10T 29/49124* (2015.01)

(58) Field of Classification Search
CPC .................. A61B 5/14507; A61B 5/1477
See application file for complete search history.

(56) References Cited

U.S. PATENT DOCUMENTS

| 3,912,614 A | 10/1975 | Spracklen |
| 4,874,500 A | 10/1989 | Madou |

(Continued)

FOREIGN PATENT DOCUMENTS

| CN | 85107234 | 4/1987 |
| CN | 1322254 | 11/2001 |

(Continued)

OTHER PUBLICATIONS

Written Opinion corresponding to International Patent Application No. PCT/US2006/049039, European Patent Office, dated Jul. 23, 2007, 5 pages.

(Continued)

*Primary Examiner* — Meredith Weare
(74) *Attorney, Agent, or Firm* — Nixon Peabody LLP (57) ABSTRACT

An electrochemical sensor system is adapted to assist in determining an analyte concentration of a fluid. The electrochemical sensor system comprises a substrate, conductive material and a hydrogel or liquid. The substrate having porosity therethrough. The conductive material includes at least one electrode. The at least one electrode is coupled to the substrate. The at least one electrode has a first surface and an opposing second surface. The hydrogel or liquid is adapted to assist in carrying the analyte of the fluid to the first and second surfaces of the at least one electrode.

8 Claims, 7 Drawing Sheets

Related U.S. Application Data (60) Provisional application No. 60/754,140, filed on Dec. 27, 2005.

(51) Int. Cl.
*A61B 5/145* (2006.01)
*C12Q 1/00* (2006.01)

(56) References Cited

U.S. PATENT DOCUMENTS

| | | | |
|---|---|---|---|
| 5,183,549 A | 2/1993 | Joseph | |
| 5,393,401 A | 2/1995 | Knoll | |
| 5,468,374 A | 11/1995 | Knoll | |
| 6,551,496 B1 | 4/2003 | Moles | |
| 9,668,683 B2* | 6/2017 | Brenneman | A61B 5/1477 |
| 2001/0003045 A1 | 6/2001 | Davis | |
| 2003/0088166 A1 | 5/2003 | Say | |
| 2004/0167383 A1 | 8/2004 | Kim | |
| 2005/0027179 A1 | 2/2005 | Berner | |
| 2005/0158704 A1 | 7/2005 | Tyvoll | |
| 2005/0211572 A1 | 9/2005 | Buck | |
| 2006/0094946 A1 | 5/2006 | Kellogg | |
| 2006/0257996 A1 | 11/2006 | Simpson | |

FOREIGN PATENT DOCUMENTS

| | | |
|---|---|---|
| CN | 1439058 | 8/2003 |
| CN | 1531650 | 9/2004 |
| JP | 61-025541 | 2/1986 |
| JP | 63-135131 | 6/1988 |
| JP | 3251229 | 11/1991 |
| JP | 4227235 | 8/1992 |
| JP | 2008-518662 | 6/2008 |
| JP | 2008-519009 | 6/2008 |
| WO | WO 2006/050032 | 5/2006 |

OTHER PUBLICATIONS

International Search Report corresponding to International Patent Application No. PCT/US2006/049039, European Patent Office, dated Jul. 23, 2007, 3 pages.

* cited by examiner

*Fig. 12*

METHOD OF DETERMINING AN ANALYTE CONCENTRATION OF A FLUID

CROSS-REFERENCE TO RELATED APPLICATIONS

This application is a division of U.S. patent application Ser. No. 12/087,087, filed Jan. 27, 2009, now allowed, which is a nationalization of International Application No. PCT/US2006/049039, filed Dec. 21, 2006, which claims priority to U.S. Provisional Application No. 60/754,140, filed Dec. 27, 2005, each of which is hereby incorporated by reference herein in its entirety.

FIELD OF THE INVENTION

The present invention generally relates to an electrochemical sensor system and method of making the same. More specifically, the present invention relates to an electrochemical sensor system using a substrate that has porosity therethrough and a method of making of the same.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, sensors are used to test a sample of blood.

A test sensor contains biosensing or reagent material that reacts with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested. This signal is supplied to the meter via contact areas located near the rear or contact end of the sensor and becomes the measured output.

One existing process for forming an electrochemical sensor is to deposit a conductive metal onto a substrate and then use a subtractive method for removing selected portions of the deposited conductive metal. Another existing process is to print the electrode by using a conductive ink, which is an additive process. The conductive ink may contain platinized carbon, platinum or other noble metal with a carrier that includes carbon particles. In both of these existing processes, the area of the conductive metal that can be used as an electrode is limited to a single two-dimensional footprint. Since the conductive material is expensive, it is desirable for the manufacturer to use as little conductive material as necessary while still maintaining the desired functionality.

It would be desirable to have an electrochemical sensor system that reduces the amount of conductive material needed, which reduces the cost, while at the same time still maintaining the desired functionality.

SUMMARY OF THE INVENTION

According to one embodiment, an electrochemical sensor system is adapted to assist in determining an analyte concentration of a fluid. The electrochemical sensor system comprises a substrate, conductive material and a hydrogel or liquid. The substrate has porosity therethrough. The conductive material includes at least one electrode. The at least one electrode is coupled to the substrate. The at least one electrode has a first surface and an opposing second surface. The hydrogel or liquid is adapted to assist in carrying the analyte of the fluid to the first and second surfaces of the at least one electrode.

According to one method, an electrochemical sensor system is formed that is adapted to assist in determining an analyte concentration. A substrate having porosity therethrough is provided. Conductive material is added to the substrate. The conductive material has a first side and a second side. The conductive material forms at least one electrode. A hydrogel or liquid is provided. The substrate and the at least one added electrode is contacted by the hydrogel such that the analyte is adapted to contact the first side and the second side of the at least one electrode.

According to another method, an analyte concentration of a fluid is determined. An electrochemical sensor system is provided that includes a substrate, conductive material, and a hydrogel or liquid. The substrate has porosity therethrough. The conductive material is coupled to the substrate. The conductive material has a first side and a second side. The conductive material forms at least one electrode. The substrate and the at least one added electrode contact the hydrogel such that the analyte is adapted to contact the first side and the second side of the at least one electrode. The electrochemical sensor system is placed on the skin. The analyte concentration of the fluid is determined.

BRIEF DESCRIPTION OF THE DRAWINGS

FIG. 2b shows an enlarged side view of an electrochemical sensor with a hydrogel of FIG. 2a.

FIG. 2c is an enlarged cross-sectional view taken generally along line 2c-2c of FIG. 2a.

DETAILED DESCRIPTION OF ILLUSTRATED EMBODIMENTS

The present invention is directed to an electrochemical sensor system and a process of making the same that reduces the quantity of conductive material that is used to form the at least one electrode. By using both sides of the conductive material forming the at least one electrode, the quantity of conductive material may be reduced. When the quantity of conductive material needed is reduced, the size of the electrochemical sensor system may also be reduced. By reducing the conductive material, the cost of making the electrochemical sensor is also reduced. The electrochemical sensor system is adapted to be used with an instrument or meter to determine the concentration of an analyte.

The present invention is desirably used in a transdermal analyte system because of the cost of the conductive material. Additionally, in transdermal analyte systems, the ability to reduce the relatively large size of a working electrode is advantageous. The relatively large size of the working electrode is needed in transdermal analyte systems to give a measurable signal at the very low analyte concentrations. These very low analyte concentrations may be extracted from, for example, the interstitial fluid via a hydrogel or liquid.

The electrochemical sensor system assists in determining concentrations of analytes. Analytes that may be measured include glucose, lipid profiles (e.g., cholesterol, triglycerides, LDL and HDL), microalbumin, fructose, lactate, or bilirubin. It is contemplated that other analyte concentrations may be determined. The analytes may be in, for example, intracellular and/or intercellular fluid. Intercellular fluids include ISF (interstitial fluid), a blood plasma sample, a blood serum sample, and exudate. As used within this application, the term "concentration" refers to an analyte concentration, activity (e.g., enzymes and electrolytes), titers (e.g., antibodies), or any other measure concentration used to measure the desired analyte.

The electrochemical sensor system may include an appropriately selected enzyme to react with the desired analyte or analytes to be tested. For example, an enzyme that may be used to react with glucose is glucose oxidase. It is contemplated that other enzymes may be used to react with glucose such as glucose dehydrogenase.

The electrochemical sensor system is adapted to assist in determining an analyte concentration and comprises a substrate, conductive material and a hydrogel or liquid. The conductive material is used to form the at least one electrode. The hydrogel or liquid assists in carrying the analyte to the conductive material.

Figure 1:
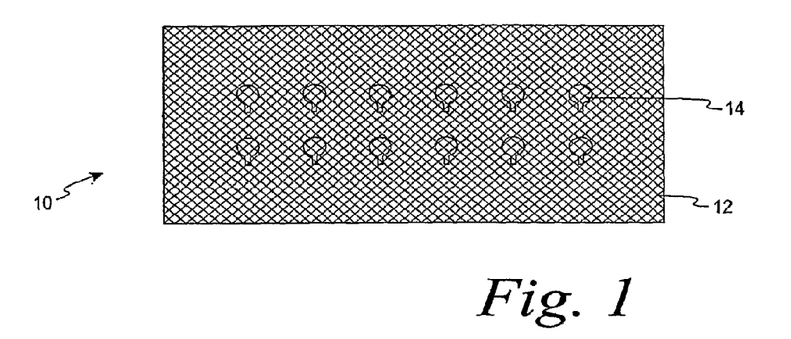
FIG. 1 is a continuous sheet of an electrochemical sensor that includes a continuous substrate with conductive material according to one embodiment.

A non-limiting example of a continuous sheet of an electrochemical sensor is shown in FIG. 1. FIG. 1 depicts a continuous sheet of an electrochemical sensor 10 that includes a continuous substrate 12 with a plurality of discrete conductive material areas 14 that has been added to the continuous substrate 12. The continuous substrate 12 depicted in FIG. 1 is a scrim, screen, woven material or a combination thereof. The continuous sheet of the electrochemical sensor may then be cut to provide for individual electrochemical sensors.

Figure 2A:
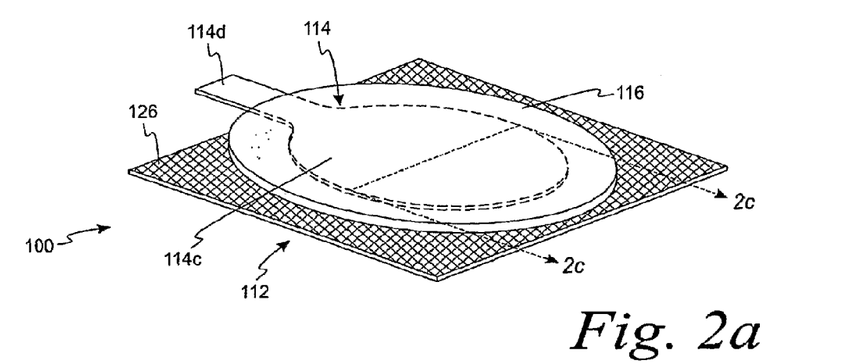
FIG. 2a is a top perspective view of an electrochemical sensor with a hydrogel according to one embodiment.
Figure 2B:
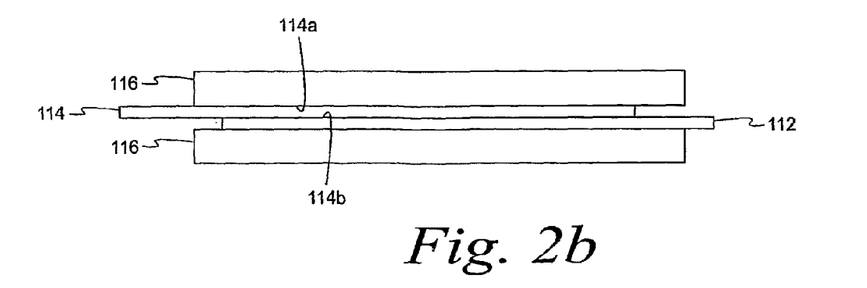
Figure 2C:
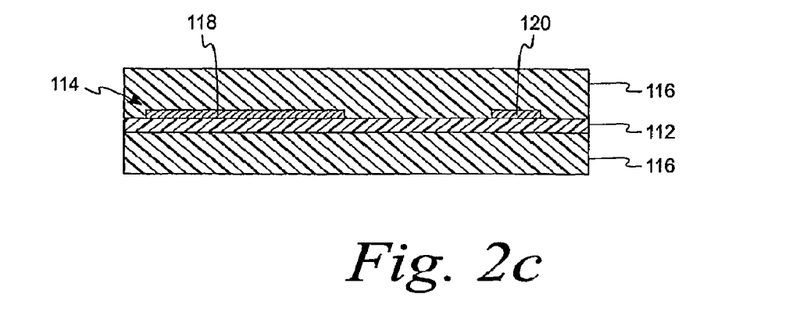

Referring to FIGS. 2a-c, a non-limiting example of an electrochemical sensor system 100 is shown. The electrochemical sensor system 100 includes a substrate 112, conductive material 114, and a hydrogel or liquid 116. The conductive material 114 is coupled to the substrate 112. More specifically, as shown in FIG. 2b, the conductive material 114 is attached to the substrate 112. The hydrogel 116, as viewed in FIG. 2b, is located both above and below the conductive material 114 and the substrate 112.

The substrate 112 to be used in the electrochemical sensor system 100 is porous and includes sufficient strength to support the conductive material 114. The substrate may comprise a screen, scrim, woven material, or combinations thereof. It is contemplated that the substrate may be of other forms that are sufficient porous so as to allow the hydrogel or liquid to move therethrough and contact both sides 114a, 114b of the conductive material 114. For example, a solid, non-porous material may have at least one and more desirably a plurality of apertures formed therein that allows both sides of the conductive material to be accessible to the hydrogel or liquid. By having both sides of the conductive material accessible to the hydrogel or liquid, the time required for the analyte to reach the conductive material is reduced.

In one embodiment, the substrate 112 forms a plurality of apertures 126 (see FIG. 2a) therein. The apertures may be of various sizes and shapes, but are formed to allow the hydrogel or fluid to contact the conductive material 114 on both sides 114a, 114b. The apertures are desirably sized and shaped to correspond with the analyte that is to flow through the apertures 126. This would include the desirable amount and rate of the analyte flow.

By using both sides 114a, 114b of the conductive material 114, the overall footprint and the amount of conductive material required to form the at least one electrode is reduced. Thus, by allowing the hydrogel or liquid to contact both sides of the conductive material, the electrodes may be of a smaller size, which leads to making a smaller electrochemical sensor. It is contemplated, however, that the substrate may form exactly one aperture therethrough that allows the hydrogel or fluid to contact both surfaces of the conductive material.

The substrate may be made from a variety of materials. For example, the substrate may be formed from a polymeric material. Non-limiting examples of polymeric materials that may be used in forming the substrate include polyethylenes, polypropylenes, polyethylene terephthlates (PET), polyethers, polycarbonates, or combinations thereof. The polymeric material may be pre-formed with apertures or the polymeric material may have apertures formed therethrough in later processing.

It is contemplated that other polymeric materials may be used in forming the substrate such as cellulose material and porous ceramic. If a solid non-porous material is used, then the material may be porous by pre-forming apertures therethrough. Alternatively, the ceramic material may be formed in a manner that forms apertures therethrough in later processing. The substrate may be formed of a metallic material, but this is often undesirable because such a substrate would likely need to include an insulating dielectric layer.

The substrate may also be used to create an electric field pattern that prevents or inhibits interfering materials from getting to the analysis area. By reducing the interfering materials, the determination of the analyte concentration may be improved. In this embodiment, the substrate creates a positive or negative charged surface that assists in preventing or inhibiting interfering materials from getting to the analysis area. In the case of determining the analyte concentration of glucose, such a field would have little or no effect with glucose because glucose does not have a charge. It is very desirable for the electric field pattern to have little or no effect on the analyte concentration that is being determined.

Such electric field patterns may be applied to the substrate (e.g., lower portion of the substrate closest to the skin) that prevent or inhibit interfering compounds from coming through based on charged properties. In this embodiment, the analysis typically occurs on an opposing surface of the substrate (e.g., upper portion of the substrate that is furthest away from the skin). The electric field patterns in one embodiment may be located in apertures formed in the substrate.

The electric field patterns may be applied to the substrate by, for example, printing or coating methods. In one embodiment, exactly one side of the substrate is printed or coated with binding materials that would bind interfering materials. It is contemplated that both sides of the substrate may include such binding materials.

In another embodiment, the substrate may include an enzyme that is used to assist in determining the analyte concentration. In this embodiment, the enzyme may be coated on one side of the substrate, while the conductive material is located on an opposing side. In this embodiment, the intermediate in the analysis process would be produced in close proximity to where the next step of the analysis process occurs. This increases the conversion efficiency and, thus, increases the signal observed at the sensor. For example, if the analyte to be determined is glucose using the enzyme glucose oxidase, then peroxide would form at the substrate surface with the glucose oxidase coating. It is desirable for the coating to cover the substrate in such a manner that the substrate remains porous. For example, if the substrate is a scrim or a screen, the coating is added so as to leave the plurality of apertures formed in the scrim or screen partially open so as to assist the hydrogel or fluid in contacting both sides of the conductive material.

It is also contemplated that the substrate may include a mediator that is an electron acceptor and assists in generating a current that corresponds to the analyte concentration. It is also contemplated that other additives may be added to the substrate to assist in facilitating the determination of the selected analyte.

Figure 3:
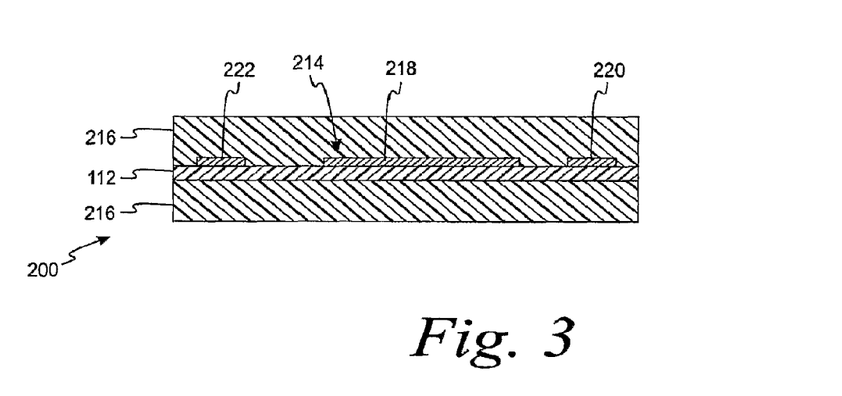
FIG. 3 is a cross-sectional view of an electrochemical sensor system with three electrodes according to one embodiment.

The conductive material 114 is added to the substrate 112 and forms at least one electrode. Typically, the conductive material 114 forms a plurality of electrodes. For example, in FIG. 2c, the conductive material 114 forms a plurality of electrodes, which includes a working electrode 118 and a counter electrode 120. The working electrode 118 and a counter electrode 120 create an electrochemical current that can flow when these electrodes are electrically connected and a potential is created between them. The plurality of electrode may include three or more electrodes such as a counter electrode, a working electrode, and a reference electrode. An example of an electrochemical sensor system that includes three electrodes is depicted in FIG. 3. Specifically, an electrochemical sensor system 200 of FIG. 3 includes the substrate 112, conductive material 214 and a hydrogel 216. The conductive material 214 includes a working electrode 218, a counter electrode 220 and a reference electrode 222. It is contemplated that more or less electrodes can be formed using the conductive material.

The electrons created by the enzymatic reaction flow through the working electrode to a meter or instrument that measures the magnitude of the current flow. The counter electrode provides a fixed potential against which the working electrode is controlled. The counter electrode may also be used to complete the electrical circuit.

Figure 4:
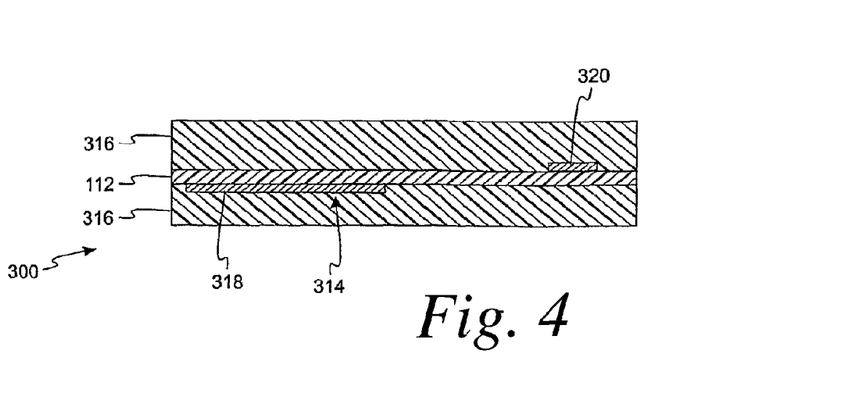
FIG. 4 is a cross-sectional view of an electrochemical sensor system with two electrodes according to one embodiment.

The conductive material may be added on a surface of the substrate in one embodiment. It is contemplated that the added conductive material, if printed for example, may be added on a surface of the substrate and also penetrate the surface of the substrate. Examples of the conductive material being added on a surface of a substrate are shown in FIGS. 2c, 3 and 4. In FIG. 4, an electrochemical sensor 300 is shown that includes the substrate 112, conductive material 314, and a hydrogel 316. The conductive material 314 includes a working electrode 318 and a counter electrode 320 in which the working and counter electrodes 318, 320 are located on opposing sides of the substrate 112.

Figure 5:
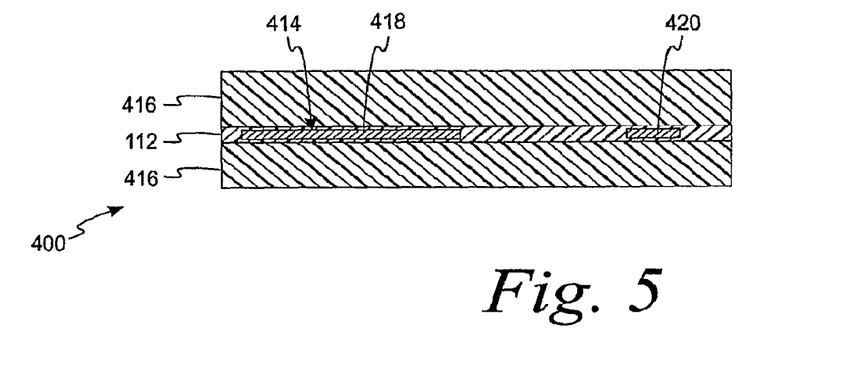
FIG. 5 is a cross-sectional view of an electrochemical sensor system with two electrodes according to another embodiment.

In another embodiment, the conductive material may be located at least partially within the substrate. Referring to FIG. 5, an electrochemical sensor 400 is shown that includes the substrate 112, conductive material 414 and a hydrogel 416. The conductive material 414 is located at least partially within the substrate 112. More specifically, the conductive material 114, which includes a working electrode 418 and a counter electrode 420, is located within the substrate 112.

Figure 6:
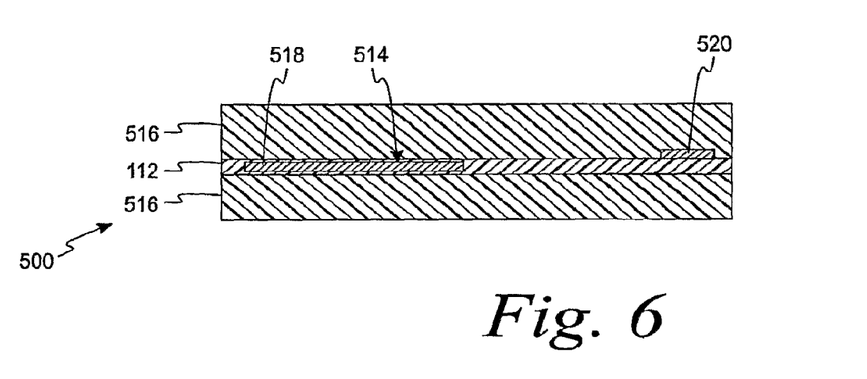
FIG. 6 is a cross-sectional view of an electrochemical sensor system with two electrodes according to a further embodiment.

It is contemplated that the conductive material may be located both on the substrate and within the substrate. For example, in FIG. 6, an electrochemical sensor system 500 is shown that includes the substrate 112, conductive material 514 and a hydrogel 516. The conductive material 514 includes a working electrode 518 and a counter electrode 520. The working electrode 518 is located within the substrate 112 and the counter electrode 520 is located on the substrate 112.

Figure 7:
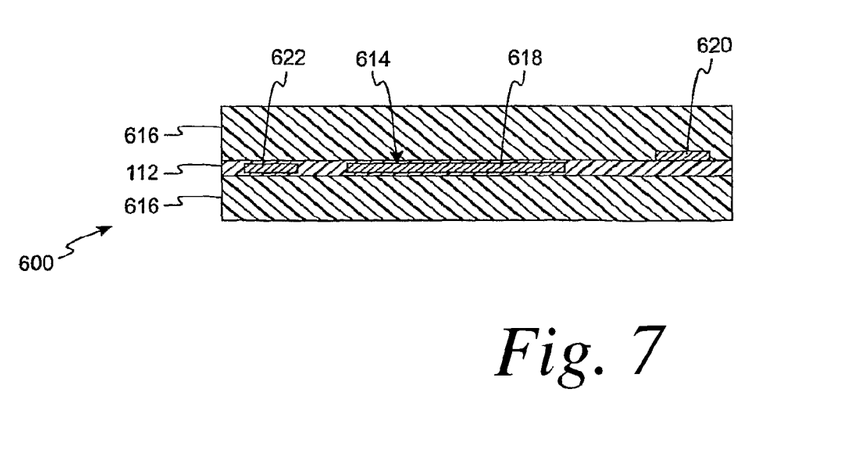
FIG. 7 is a cross-sectional view of an electrochemical sensor system with three electrodes according to a further embodiment.
Figure 8A:
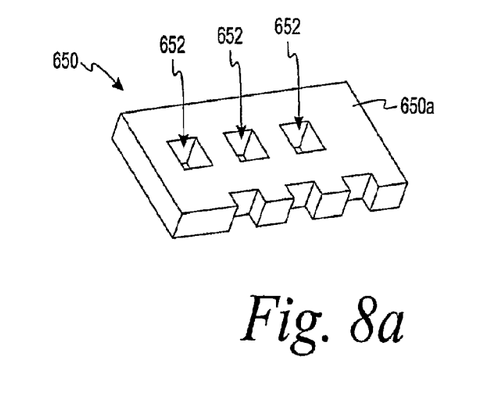
FIG. 8a is a top perspective view of a portion of a substrate according to one embodiment.
Figure 8B:
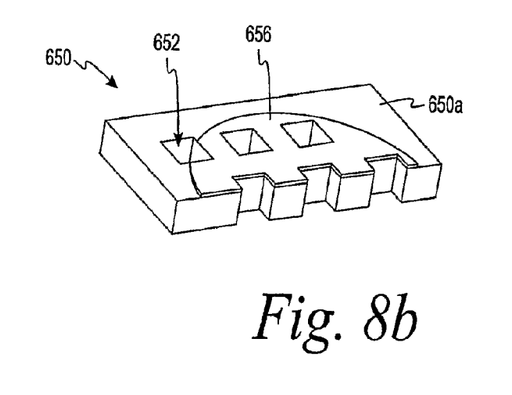
FIG. 8b is a top perspective view of the substrate of FIG. 8a with an electrode added to one side according to one embodiment.
Figure 8C:
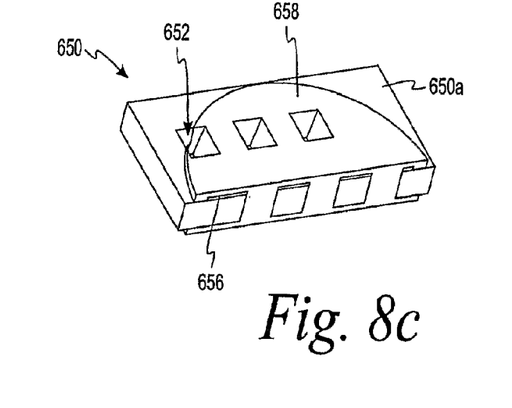
FIG. 8c is a top perspective view of FIG. 8b with a hydrogel or fluid added according to one embodiment.
Figure 8D:
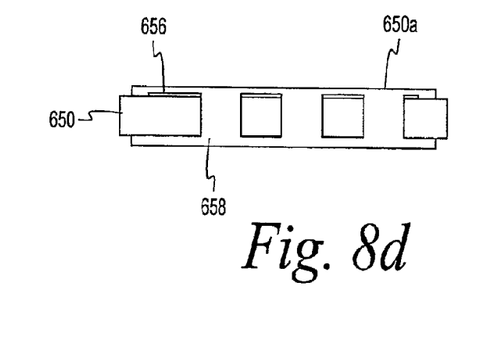
FIG. 8d is a side view of FIG. 8c.

In another embodiment, an electrochemical sensor system 600 of FIG. 7 includes the substrate 112, conductive material 614 and hydrogel 616. The conductive material 614 includes a working electrode 618 and a counter electrode 620 and a reference electrode 622. The working and reference electrodes 618, 622 are located within the substrate 112 and the counter electrode 620 is located on substrate 112.

The conductive material may be a metallic material or other conductive material such as platinum carbon. Non-limiting examples of conductive metallic materials include copper, nickel, gold, platinum, palladium, rhodium or combinations thereof. The thickness of the conductive metallic material is generally from about 10 to about 10,000 Angstroms. The thickness of the conductive metallic material is more typically from about 100 to about 1,000 Angstroms.

The thickness of the conductive material may be greater than the thickness of the substrate. For example, if the conductive material is platinum carbon, then the thickness of such a conductive material is typically greater than the thickness of the substrate. It is also contemplated that the thickness of the conductive material may be less than the thickness of the substrate. For example, if a platinum coating is added to the substrate, then the thickness of such a coating is typically less than the thickness of the substrate.

The size and shape of the conductive material is shown in FIG. 2a as including a generally circular portion 114c and an extension portion 114d extending therefrom. The size and shape of the conductive material can vary from that shown in FIGS. 1, 2a. The size and shape of the conductive material is selected to facilitate the determination of the analyte concentration as well as reduce the cost associated with manufacturing the same. The size and shape of the conductive material may also be selected for other reasons. For example, if a reservoir is used to replenish the hydrogel or liquid, then the placement of the conductive material may be optimized to provide the desired porosity to carry the hydrogel or liquid from the reservoir to a skin-contacting location. A reservoir may be used if the characteristics of the hydrogel are prone to changing over the testing period, which typically includes the solvent percentage of the hydrogel being reduced over time.

In one embodiment, a hydrogel is used to assist in hydrating the skin and carrying the analyte of interest to the at least one electrode formed by the conductive material. The content of the solvent (e.g., water) in the hydrogel can vary. To increase the mechanical strength of the hydrogel 116, the hydrogel 116 is supported by the substrate 112 with the conductive material 114. Thus, the need for an additional substrate material is eliminated.

A hydrogel composition is defined herein as including a cross-linked polymer gel. The hydrogel composition generally comprises at least one monomer and a solvent. The solvent is typically substantially biocompatible with the skin. Non-limiting examples of solvents that may be used in the hydrogel composition include water and a water mixture. The amount of solvent in the hydrogel is generally from about 10 to about 95 weight percent and may vary depending on the monomer amount, crosslinking, and/or the desired composition of the gel.

The amount of hydrogel that is selected is based on the need to provide a hydrated skin and having the hydrogel remain in intimate contact with the skin. One disadvantage of using a large amount of hydrogel in the electrochemical sensor system is the potential impact on the lag time of the analyte getting to the at least one electrode and, thus, the potential impact on the analysis time. By having an electrochemical sensor system in which the hydrogel is capable of contacting both sides of at least one electrode, the effect of impacting the lag times of the analyte getting to the electrodes is reduced. It is advantageous to have the hydrogel capable of contacting both sides of a plurality of electrodes. By having an electrochemical sensor system that is able to contact both sides of at least one electrode and desirably a plurality of electrodes, the present invention has the ability to use a greater amount of water in the hydrogel.

It is also contemplated that a liquid may be used to assist in hydrating the skin and carrying the analyte of interest to the at least one electrode formed by the conductive material. It is contemplated that the liquid or the hydrogel may be located in a material matrix. In such an embodiment, the material matrix must allow the movement of the liquid or hydrogel to the at least one electrode.

It is also contemplated that the mediator may be located in the hydrogel or liquid. To maximize efficiency, the distribution of the mediator may be structured. It is also contemplated that other components may be located within the hydrogel or liquid.

Referring to FIGS. 8-10, a single electrode is shown in different embodiments on a portion of the substrate. Referring first to FIGS. 8a-8d, a substrate 650 is shown with a plurality of apertures formed 652 therein. As shown in FIG. 8b, the substrate 650 has a single electrode 656 that is located on a surface 650a of the substrate 650. A hydrogel or liquid 658 is added over the substrate 650 and electrode 656 as shown in FIGS. 8c and 8d. The hydrogel or liquid 658 extends into and through the plurality of apertures 652. In this embodiment, the electrode 656 does not extend into the plurality of apertures 652. It is contemplated, however, that the electrode may extend into the plurality of apertures.

Figure 9A:
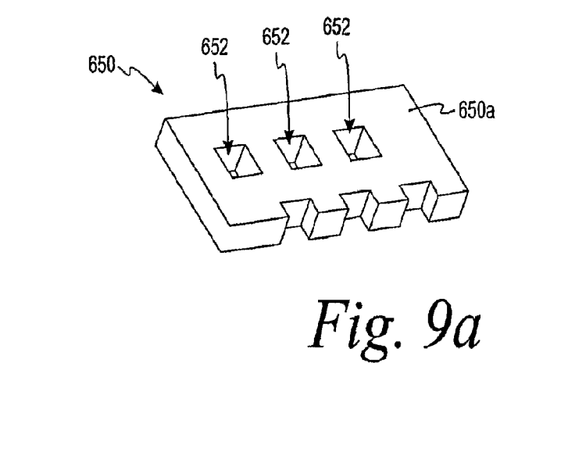
FIG. 9a is a top perspective view of a portion of a substrate according to one embodiment.
Figure 9B:
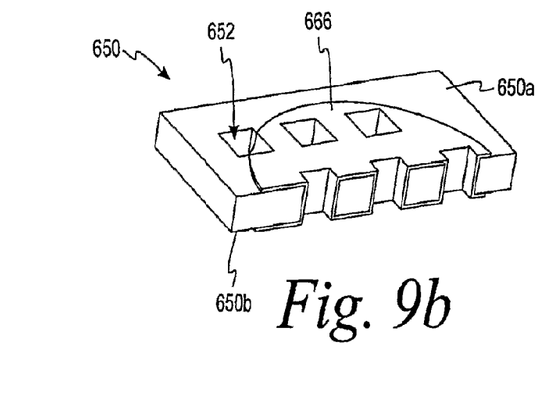
FIG. 9b is a top perspective view of the substrate of FIG. 9a with an electrode added to both sides according to one embodiment.
Figure 9C:
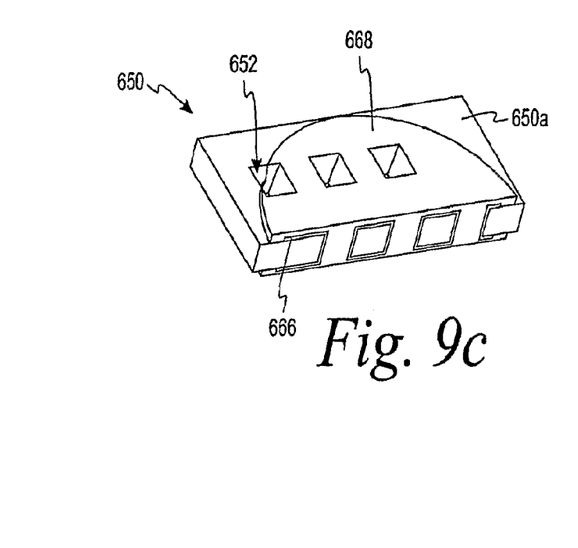
FIG. 9c is a top perspective view of FIG. 9b with a hydrogel or fluid added according to one embodiment.
Figure 9D:
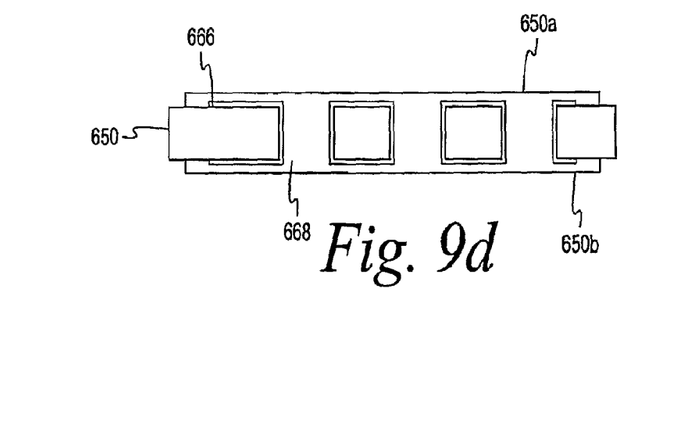
FIG. 9d is a side view of FIG. 9c.

Referring to FIGS. 9a-9d, a substrate 650 is shown with a plurality of apertures formed 652 therein. As shown in FIG. 9b, the substrate 650 has a single electrode 666 that is located on surfaces 650a, 650b of the substrate 650. More specifically, the electrode 666 is located on opposing surfaces 650a, 650b of the substrate 650 and extends through the plurality of apertures 652. The electrode 666 substantially fills the plurality of apertures 652. It is contemplated that the electrode may partially fill the plurality of apertures such that an electrical connection is still established therethrough. A hydrogel or liquid 668 is added over the substrate and electrode 666 as shown in FIGS. 9c and 9d. It is contemplated that the hydrogel or liquid may extend into and through the plurality of apertures if the electrode 666 does not substantially fill the plurality of apertures 652.

Figure 10A:
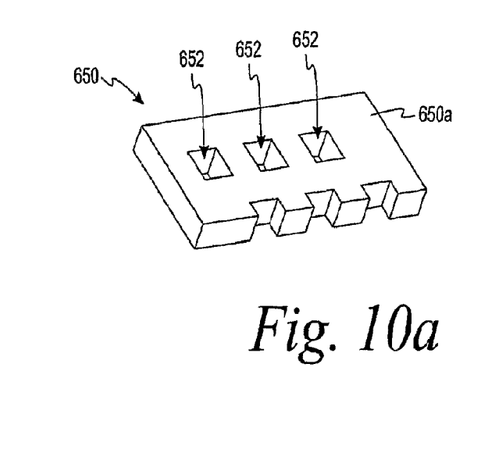
FIG. 10a is a top perspective view of a portion of a substrate according to one embodiment.
Figure 10B:
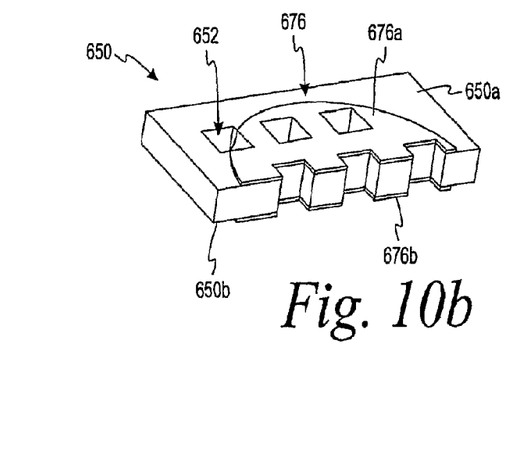
FIG. 10b is a top perspective view of the substrate of FIG. 10a with an electrode added to two sides according to another embodiment.
Figure 10C:
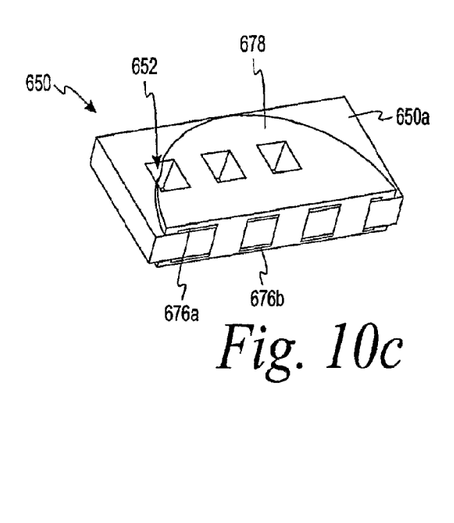
FIG. 10c is a top perspective view of FIG. 10b with a hydrogel or fluid being added according to another embodiment.
Figure 10D:
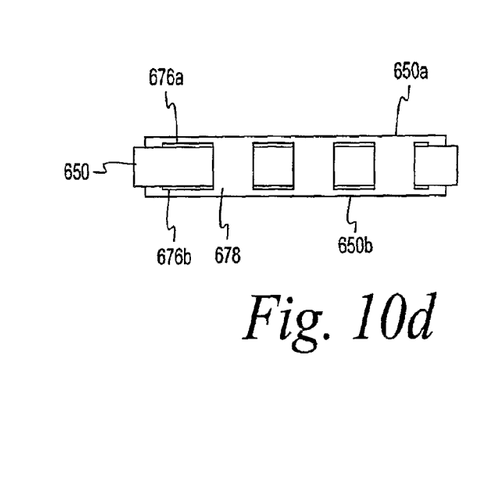
FIG. 10d is a side view of FIG. 10c.

Referring to FIGS. 10a-10d, a substrate 650 is shown with a plurality of apertures formed 652 therein. As shown in FIG. 10b, the substrate 650 has a single electrode 676 that includes a first electrode section 676a and a second electrode section 676b. The first electrode section 676a is located on surface 650a, while the second electrode section 676b is located on surface 650b of the substrate 650. Thus, the first and second electrode sections 676a, 676b do not extend through the plurality of apertures 652. It is contemplated that the electrode sections may extend partially into the plurality of apertures. A hydrogel or liquid 678 is added over the substrate and electrode sections 676a, 676b as shown in FIGS. 10c and 10d. The hydrogel or liquid 680 extends into and through the plurality of apertures 652.

In the embodiments depicted in FIGS. 8-10, only a single electrode (e.g., a working electrode) has been depicted. It is contemplated that the working electrode, counter electrode or any other electrode may be on both sides of the substrate, on only one side of the substrate, or on opposite sides of the substrate.

According to one method, an electrochemical sensor system is formed that is adapted to assist in determining an analyte concentration. A substrate with a porosity therethrough (e.g., substrate 112) in one embodiment comprises a screen, scrim, woven material or combinations thereof. As discussed above, the substrate 112 forms apertures therein. Conductive material (e.g., conductive material 114) is added to the substrate. The conductive material has a first side and a second side and forms at least one electrode. A hydrogel (e.g., hydrogel 116) or liquid is provided. The substrate with the plurality of electrodes contacts the hydrogel such that the analyte is adapted to contact the first side and the second side of the at least one electrode. The conductive material as shown in, for example, FIG. 3 is placed in a general center of the hydrogel.

The conductive material may be added to the substrate by different techniques. In one method, the conductive material is added to the substrate by sputtering. The sputtering process may deposit metals such as platinum, copper, nickel, gold, palladium, rhodium and combinations thereof. It is contemplated that other conductive materials may be sputtered to the substrate. The sputtering process places conductive material on at least one surface of the substrate and the conductive material may penetrate the substrate to some extent. It is contemplated that the sputtering process may be used to place conductive material on both sides of the substrate.

In another method, the conductive material is added to the substrate by printing. The printing may be performed by using platinum or platinized carbon inks. It is contemplated that other conductive materials may be printed to the substrate. In a typical printing process, the conductive material is placed on at least one surface and the conductive material may penetrate the substrate to some extent. It is contemplated that the printing process may add conductive material on both sides of the substrate.

It is contemplated that other methods may be used in adding the conductive material to the substrate. For example, the conductive material may be added to the substrate using electroplating or powder coating.

In one embodiment, all of the electrodes are added to the substrate. It is contemplated that less than all of the electrodes are added to the substrate. For example, one electrode may be added to the substrate while the other electrode is located near the analysis area.

Figure 11:
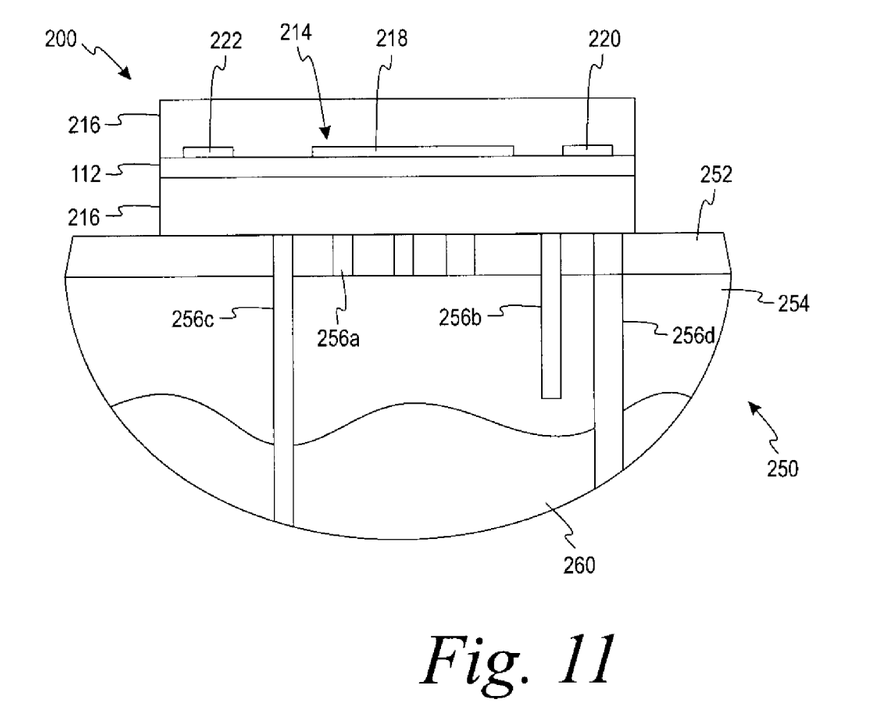
FIG. 11 is the electrochemical sensor system of FIG. 3 being placed over a surface of the skin according to one embodiment.

The present invention may be used in a transdermal approach in which the analyte is continuously monitored. As shown in FIG. 11, the electrochemical system 200 of FIG. 3 is shown in a transdermal application. Specifically, the electrochemical system 200 is shown being placed above a stratum corneum layer 252 of epidermis 254 in FIG. 11. The stratum corneum layer 252 has a plurality of channels 256a-d formed therein. The channels 256a-d may be of different sizes and depths depending on the analyte being tested and the location of the analyte in the skin 250.

The plurality of channels 256a-d may be formed by different methods such as a laser-initiated opening, a lance, or a pressure member adapted to apply pressure to and stretch the skin 250 in preparation for forming a tear in the skin. It is contemplated that other methods may be used such as using pumas or gels, tape stripping or various skin abrasion methods. The analyte of interest may be located in the epidermis 254 or dermis layer 260. For example, one analyte (e.g., glucose) is located in the dermis layer 260. Glucose, for example, diffuses through the fluid paths that are established in the plurality of channels 252 formed in the stratum corneum layer 252. The hydrogel, with generally high water content, maintains a fluid channel for diffusion of the analyte of interest.

The electrochemical sensor system may also be used to continuously monitor analytes in the ISF. Such analytes may be located on the skin. The analytes are typically located in the transdermal region (epidermis, dermis or subcutaneous tissue) of the skin. The analytes are brought to the skin surface using diffusional channels. The analysis is then carried out at the surface of the skin using several analytical techniques.

Figure 12:
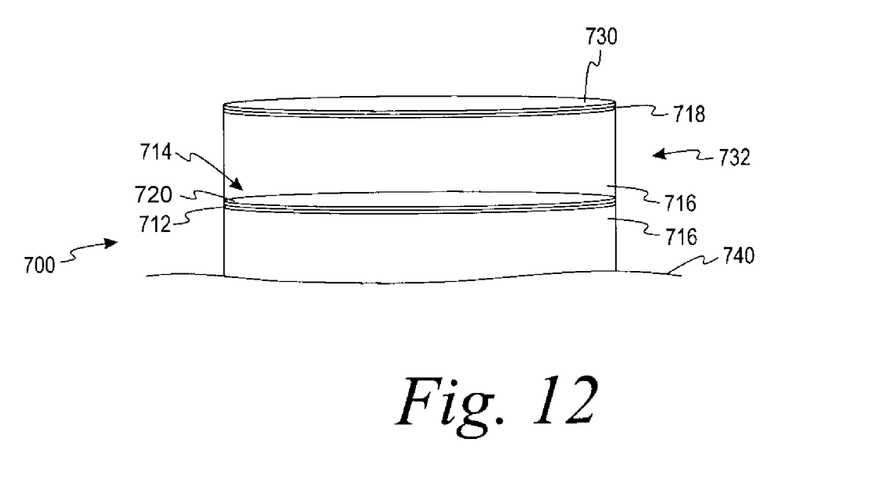
FIG. 12 is an electrochemical sensor system that is used in a coulometric analysis approach according to one embodiment.

It is contemplated that an electrochemical sensor system of the present invention may use a coulometric analysis approach. The coulometric analysis approach would likely increase the sensitivity of the assay in that more signal would be generated. One example of an electrochemical sensor system that uses a coulometric analysis approach is shown in connection with FIG. 12. Electrochemical sensor system 700 of FIG. 12 includes a substrate 712 with conductive material 714, hydrogel 716 and a working electrode 718. The electrochemical sensor system 700 is placed on skin 740. The conductive material 714 includes a counter electrode 720. In this embodiment, the working electrode 718 is printed on backing material 730. The backing material 730 may be made of a polymeric backing material. The coulometric analysis is conducted between the counter electrode 720 on the substrate 712 and the working electrode 718. The coulometric analysis is based on the conversion of all of the analyte in a defined volume. The defined area of FIG. 12 is the area 732 between the substrate 712/counter electrode 720 and the working electrode 718. This area 732 is predominately occupied by the hydrogel 716, but also contains the diffused analyte (e.g., glucose) or the conversion product of glucose. The analysis is based on the integration of the current generated over a time period.

The side of the substrate that is located away from the skin may also form the lower part of a chamber that contains a liquid such as water that forms a reservoir for the hydrogel that is below the scrim and in contact with the skin. This would assist in hydrating the hydrogel for longer periods of time. The location of the sensors on the substrate provides for significant digress of freedom in the design and materials that can be used on the opposing surface of the substrate. A highly hydrated thick hydrogel may be used so as to provide a reservoir for the hydrogel in contact with the skin. The increased thickness would have little or no impact on the lag times.

Embodiment A

An electrochemical sensor system adapted to assist in determining an analyte concentration of a fluid, the electrochemical sensor system comprising:

a substrate having porosity therethrough;

conductive material including at least one electrode, the at least one electrode being coupled to the substrate, the at least one electrode having a first surface and an opposing second surface; and a hydrogel or liquid being adapted to assist in carrying the analyte of the fluid to the first and second surfaces of the at least one electrode.

Embodiment B

The system of embodiment A wherein the substrate is a screen, scrim, woven material or solid material with apertures.

Embodiment C

The system of embodiment B wherein the substrate is a screen.

Embodiment D

The system of embodiment B wherein the substrate is a scrim.

Embodiment E

The system of embodiment B wherein the substrate has an electric field pattern.

Embodiment F

The system of embodiment B wherein the substrate comprises polymeric material, cellulose material or porous ceramic.

Embodiment G

The system of embodiment A wherein the porosity of the substrate includes a plurality of apertures formed therethrough.

Embodiment H

The system of embodiment A wherein the at least one plurality of electrode is a plurality of electrodes, the plurality of electrodes including a working electrode and a counter electrode.

Embodiment I

The system of embodiment A wherein the at least one electrode is located on a surface of the substrate.

Embodiment J

The system of embodiment A wherein a portion of the at least one electrode is located within the substrate.

Embodiment K

The system of embodiment A wherein the conductive material is metallic.

Embodiment L

The system of embodiment A wherein the at least one electrode has a first section and a second section, the first section having the first surface and the second section having the opposing second surface.

Embodiment M

The system of embodiment A wherein the porosity of the substrate includes at least one aperture being formed therethrough, the conductive material substantially filling the at least one aperture.

Embodiment N

The system of embodiment A wherein the electrochemical sensor system uses a hydrogel.

Embodiment O

The system of embodiment N wherein the hydrogel is a cross-linked polymer.

Embodiment P

The system of embodiment A wherein the electrochemical sensor system uses a liquid.

Embodiment Q

The system of embodiment A wherein the hydrogel or liquid is in a material matrix.

Embodiment R

The system of embodiment A wherein the electrochemical sensor system is a coulometric system.

Embodiment S

The system of embodiment A wherein the electrochemical sensor system is an amperometric system.

Embodiment T

The system of embodiment A wherein the electrochemical sensor system further includes an enzyme, the enzyme being glucose oxidase or glucose dehydrogenase.

Process U

A method of forming an electrochemical sensor system that is adapted to assist in determining an analyte concentration, the method comprising the acts of:
 providing a substrate having porosity therethrough;
 adding conductive material to the substrate, the conductive material having a first side and a second side, the conductive material forming at least one electrode;
 providing a hydrogel or liquid; and
 contacting the substrate and the at least one added electrode with the hydrogel such that the analyte is adapted to contact the first side and the second side of the at least one electrode.

Process V

The method of process U wherein the conductive material is placed in a general center of the hydrogel or the liquid.

Process W

The method of process U wherein the conductive material is added to the substrate by sputtering.

Process X

The method of process U wherein the conductive material is added to the substrate by printing.

Process Y

The method of process U wherein the analyte is glucose.

Process Z

The method of process U wherein the substrate is a screen, scrim, woven material or solid material with apertures.

Process AA

The method of process Z wherein the substrate is a scrim.

Process BB

The method of process U wherein the substrate comprises polymeric material, cellulose material or porous ceramic.

Process CC

The method of process U wherein the porosity of the substrate includes a plurality of apertures formed therethrough.

Process DD

The method of process U wherein the at least one plurality of electrode is a plurality of electrodes, the plurality of electrodes including a working electrode and a counter electrode.

Process EE

The method of process U wherein the at least one electrode is located on a surface of the substrate.

Process FF

The method of process U wherein a portion of the at least one electrode is located within the substrate.

Process GG

The method of process U wherein at least one of the electrode has a first section and a second section, the first section having the first surface and the second section having the opposing second surface.

Process HH

The method of process U wherein the porosity of the substrate includes at least aperture being formed therethrough, the conductive material substantially filling the at least one aperture.

Process II

The method of process U wherein the electrochemical sensor system uses a hydrogel.

Process JJ

The method of process II wherein the hydrogel is a cross-linked polymer.

Process KK

The method of process U wherein the electrochemical sensor system uses a liquid.

Process LL

The method of process U wherein the electrochemical system is a coulometric system.

Process MM

The method of process U wherein the electrochemical system is an amperometric system.

Process NN

A method of determining an analyte concentration of a fluid, the method comprising the acts of:
providing an electrochemical sensor system including a substrate, conductive material, a hydrogel or liquid, the substrate having porosity therethrough, the conductive material being coupled to the substrate, the conductive material having a first side and a second side, the conductive material forming at least one electrode, the substrate and the at least one added electrode being contacted with the hydrogel such that the analyte is adapted to contact the first side and the second side of the at least one electrode;
placing the electrochemical sensor system on the skin; and
determining the analyte concentration of the fluid.

Process OO

The method of process NN wherein the analyte is glucose.

Process PP

The method of process NN wherein the substrate is a screen, scrim, woven material or solid material with apertures.

Process QQ

The method of process NN wherein the porosity of the substrate includes a plurality of apertures formed therethrough.

Process RR

The method of process NN wherein the at least one plurality of electrode is a plurality of electrodes, the plurality of electrodes including a working electrode and a counter electrode.

Process SS

The method of process NN wherein the electrochemical sensor system uses a hydrogel.

Process TT

The method of process NN wherein the electrochemical sensor system uses a liquid.

Process UU

The method of process NN wherein the fluid is an intercellular fluid.

Process VV

The method of process UU wherein the fluid is interstitial fluid.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined by the appended claims.

The invention claimed is:
1. A method of determining an analyte concentration of a fluid, the method comprising the acts of:
providing an electrochemical sensor system including:
a substrate having porosity including at least one aperture extending through the substrate, an enzyme coupled to the substrate, the enzyme being configured to chemically react with the analyte in the fluid, at least one conductive electrode coupled to the substrate, each electrode of the at least one electrode having a first surface and a second surface on the opposite side of the first surface, and a hydrogel having a first layer and a second layer, the hydrogel extending through the at least one aperture and contacting the first surface and the second surface of the at least one electrode and the substrate, the hydrogel being configured to carry the analyte of the fluid into contact with both the first surface and the second surface of the at least one electrode, with the at least one electrode and the substrate being sandwiched between the first layer and the second layer of the hydrogel;

placing the electrochemical sensor system on the skin; and determining the analyte concentration of the fluid.

2. The method of claim 1, wherein the analyte is glucose.

3. The method of claim 1, wherein the substrate is a screen, scrim, woven material or solid material with apertures.

4. The method of claim 1, wherein the porosity of the substrate includes a plurality of apertures formed therethrough.

5. The method of claim 1, wherein the at least one electrode is a plurality of electrodes, the plurality of electrodes including a working electrode and a counter electrode.

6. The method of claim 1, wherein the electrochemical sensor system uses a liquid.

7. The method of claim 1, wherein the fluid is an intercellular fluid.

8. The method of claim 7, wherein the fluid is interstitial fluid.

* * * * *